United States Patent [19]

Rosenthal et al.

[11] Patent Number: 4,849,077

[45] Date of Patent: Jul. 18, 1989

[54] PROCESS FOR SOLID PHASE-SEQUENCING OF NUCLEIC ACID FRAGMENTS

[75] Inventors: Andre Rosenthal, Berlin; Hans-Dieter Hunger; Horst Kagelmaker, both of Zepernick; Monika Graätschus, Berlin, all of German Democratic Rep.

[73] Assignee: Akademie der Wissenschaften der DDR, Berlin, German Democratic Rep.

[21] Appl. No.: 761,107

[22] Filed: Jul. 31, 1985

[30] Foreign Application Priority Data

| Aug. 6, 1984 [DD] | German Democratic Rep. ......... 2659974 |
| Aug. 6, 1984 [DD] | German Democratic Rep. ......... 2659982 |
| May 14, 1985 [DD] | German Democratic Rep. ......... 2763283 |

[51] Int. Cl.$^4$ .............. G01N 30/00; G01N 33/50
[52] U.S. Cl. .............. 264/182.8; 435/6; 436/94; 935/77
[58] Field of Search .............. 436/94; 435/6; 935/77, 935/78; 204/182.8

[56] References Cited

U.S. PATENT DOCUMENTS

| 4,542,102 | 9/1985 | Dattagupta et al. ............. 436/94 X |
| 4,588,682 | 5/1986 | Groet et al. ............. 935/78 X |
| 4,713,326 | 12/1987 | Dattagupta et al. ............. 436/94 X |

OTHER PUBLICATIONS

Chuvpilo et al., Khim., vol. 9, pp. 1634–1637 (1983).
Sequencing End-Labeled DNA with Base-Speific Chemical Cleavages, Author: By Allan M. Maxam and Walter Gilbert, pp. 499–561, Methods in Enzymol, 65 (1980).

Primary Examiner—Robert J. Hill, Jr.
Attorney, Agent, or Firm—Michael J. Striker

[57] ABSTRACT

A process for solid phase sequencing of nucleic acid fragments is disclosed. The object of the invention is to provide a sequencing process which enables the simultaneous sequencing of large amounts of long and short nucleic acid fragments and which is optionally automated. Thus, a solid support combining mechanical stability, anion exchange characteristics, and chemical elution of nucleic acids off the support is used. Immobilized nucleic acid fragments are chemically modified and subsequently the nucleic acid backbone is cleaved and simultaneously or subsequently said fragments are eluted by chemical means. The present invention is applied to molecular biology and gene technology.

6 Claims, 3 Drawing Sheets

PROCESS FOR SOLID PHASE-SEQUENCING OF NUCLEIC ACID FRAGMENTS

FIELD OF THE INVENTION

This invention relates to the sequential analysis of nucleic acid fragments (DNA and RNA) in molecular biology and gene technology or the sequential analysis of oligodeoxy- and oligoribonucleotides in accordance with the chemical synthesis of these segments.

BACKGROUND OF THE INVENTION

For the first time in December of 1983 a solid phase process had been described by two Russian authors (S. A. Chuvpilo and V. V. Kravchenko: Bioorg. Khim 9 (12) (1983) 1634–1637), however only for sequencing long DNA-segments and by using a commercially available DEAE-paper (DE 81 of the company Whatman). It consists of the steps: (1) immobilization of the 5'- or 3'-marked DNA-fragment on the carrier; (2) washing; (3) chemical modification reactions without excess reagent surplus (i.e., not in a reaction vessel) in accordance with Maxam and Gilbert (A. M. Maxam and W. Gilbert: Methods in Enzymol. 65 (1980) 499–560); (4) Washing; (5) Piperidine reaction under standard conditions (only 20% loss of the radioactive fragments); (6) Washing; (7) 2× elution of the fragments from the carrier with 1M NaCl at 60° C.; (8) Ethanol precipitation for precipitating the material and the 2× washing with 90% ethanol.

The disadvantages of this process are:

The very poor mechanical stability of the DE 81 paper makes the manipulation of the carrier in watery buffers very difficult (above all at high temperatures). A rapid tearing, dissolving and peeling of the carrier occurs.

The modification reactions used result in almost 100% losses in the A+G-, T+C- and C-reactions, if they are performed in reaction vessels for example, in microcentrifuge tubes with excess reagent.

Due to the poor mechanical characteristics of the DE 81 carrier, the simultaneous sequencing of large quantities of nucleic acid fragments is not possible in a reaction vessel.

In all, 8 operations are required, whereby the operation of the ethanol precipitation (no. 8) is principally not suitable for an automatic mode of operation.

Oligonucleotide=8 units cannot be sequenced in accordance with this process, since the first 5'-permanent nucleotides are lost during the repreciptation so that the sequence samples cannot be completely read.

On account of all of the described disadvantages, the described process can firstly not be automated and secondly no large quantities can be simultaneously sequenced even with a manual operation. Short nucleic acid fragments (DNA- and RNA-oligomers) cannot be sequenced at all.

Devices for performing solid phase sequencing are not known heretofore. The known sequencing process can generally be performed in commercially obtainable vessels like, for example, microcentrifuge tubes and customary laboratory glass devices. The simultaneous sequencing of a plurality of fragments is principally possible, however the operation of the process is not economical and the danger of confusing immobilized nucleic acid fragments is very large.

OBJECT OF THE INVENTION

It is an object of the invention to determine long and short nucleic acid fragments rapidly, free of confusion and in large amounts simultaneously.

SUMMARY OF THE INVENTION

Figure 1:
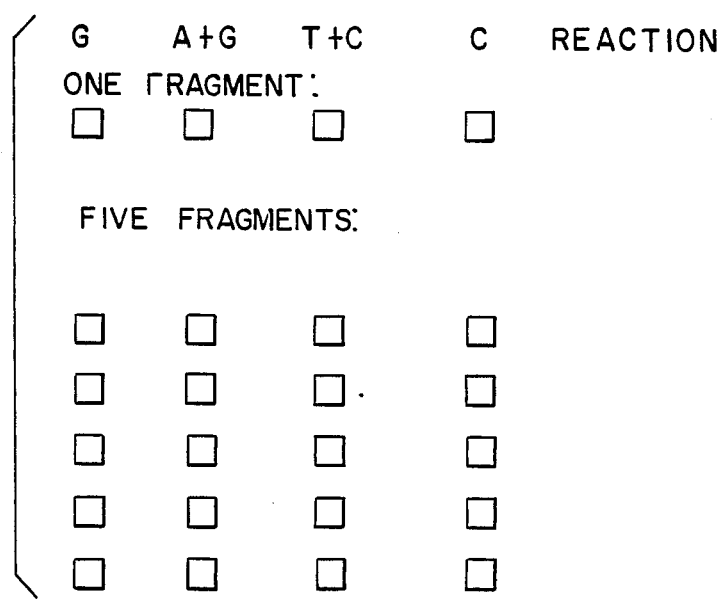
FIGS. 1 and 2 show different ways in which sample nucleic acid fragments can be attached to the face carriers for carrying out the method of the invention.

It is an object of the invention to bind nucleic acid fragments onto a solid phase in such a manner that a fully automatic manipulation or a safe manual manipulation of the immobilizates are possible.

The solution of the object of the invention is achieved in accordance with the invention with a solid phase sequencing process for nucleic acid fragments by using a novel face carrier with anion exchange characteristics and with a novel device for performing the process.

The immobilization of the marked fragment or fragments on the face carrier is performed in a known manner, for example, by placing drops thereon or by electroelution from gels (per fragment 4 carriers). These carriers are washed and subsequently the immobilized fragment or a plurality of immobilized fragments are simultaneously modified. The chemical modification reactions are performed with excess reagent surplus or without reagent surplus. When using no reagent surplus, the face carriers are placed onto a chemically inert matrix and only so much reagents are applied with micropipettes onto the face carrier that the same is only wetted.

After a washing process, the sorted fragments are individually reacted with piperidine and are extracted with chemical, ionic or electromagnetic agents.

A face carrier is used as a mechanically stable face carrier with anion exchanger characteristics which is generated by reaction of known shaped or unshaped macromolecular substances with compositions of the formula I,

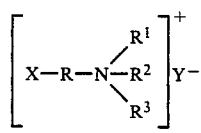

wherein

X is an NH$_2$—, OH— or SH— group

R is an alkyl group with 1–10 atoms, aromatic substance, photolytic group such as substituted o-nitrobenzene ester or substituted methylphenacylester or a heterocyclic group;

R$^1$, R$^2$ and R$^3$ are each alkyl groups with 1 to 3 carbon atoms or a hydrogen atom; and Y is halide or hydroxyl.

The macromolecular substances which are suitable for the reaction have the following composition:

5–80% by volume of a macromolecular composition

1–80% by volume of a macromolecular composition with 4,6-dihalogen-1,3,5-triazine-groupings 0.5–50% by volume 2,4,6-trihalogen-1,3,5-triazine up to 20% by volume halide if need be, up to 5% by volume of buffering substances if need be, a liquid dispersion agent.

Instead of the direct reaction of the shaped and nonshaped macromolecular substances with chemically active fillers with compositions of the formula I, one can generate advantageously compositions of formula I in situ by reaction of compositions of the formula II $$[Y\text{---}R\text{---}NH_3]^+Y^- \qquad II$$

with tertiary amines of the formula III $$\begin{array}{c} \text{---}R^1 \\ N\text{---}R^2 \\ \text{---}R^3 \end{array} \qquad III$$

In the first case, shaped macromolecular substances with chemically active fillers, for example, mechanically stable cellulose papers, fleeces and netting may be reacted, so that mechanically stable anion exchange face carriers with high binding capacities are obtained for nucleic acids of up to 120 $\mu g/cm^2$.

In the second case, nonshaped macromolecular substances can be reacted with chemically active fillers, for example, spheric, crystalline and fibrous cellulose and ion exchanges can be obtained in this manner which may be used in this shape or may be processed into shaped anion exchange face carriers with liquid dispersion agents.

If, for reaction of the shaped or nonshaped macromolecular substances with chemically active fillers, compositions of the formula I or compositions of the formula II are used in conjunction with tertiary amines, whereby R is an alkyl group with 1-10 C-atoms or an aromatic substance, anion exchangers are obtained which are chemically extractable with primary, secondary and tertiary amines. This chemical extraction has a particular meaning for the inventive solid phase sequencing process of nucleic acid fragments or for isolating of DNA-fragments made from agarose- or polyacrylamide-gel.

If, for reaction of the shaped or nonshaped macromolecular substances with chemically active fillers, compositions of the formula I are used, whereby R is substituted o-nitro-benzyl-or substituted methylphenacylester, anion exchangers are obtained which are photolytically extractable, i.e., by using electromagnetic radiation, which is advantageous with respect to automation of the process. All aforementioned ion exchangers are additionally extractable with ionic agents, i.e., with high ion strengths of the salts, for example, $NH_4HCO_3$, $(NH_4)_2CO_3$, $Et_3NHAc$, $NH_4Ac$, $K_2HPO_4$, NaCl and others.

The described anion exchangers have a high binding capacity and have an excellent mechanical stability in particular in the face shape. For this reason, the use of the shaped anion exchangers in further molecular biological and biochemical research is particularly indicated. In contrast to the customary anion exchangers, the exchangers in accordance with the invention have further extraction possibilities with chemical agents or electromagnetic radiation, in addition to the ionic extraction.

For immobilization purposes, 1 or n 5'- or 3'-labeled long or short nucleic acid fragments are applied onto 4 or 4×n individual mechanically stable face carriers (about 1 to 2×1 to 2 mm) with anion exchange characteristics.

See FIG. 1 for immobilizing one fragment and five fragments on separate face carriers for carrying out the method of the invention.

Figure 2:
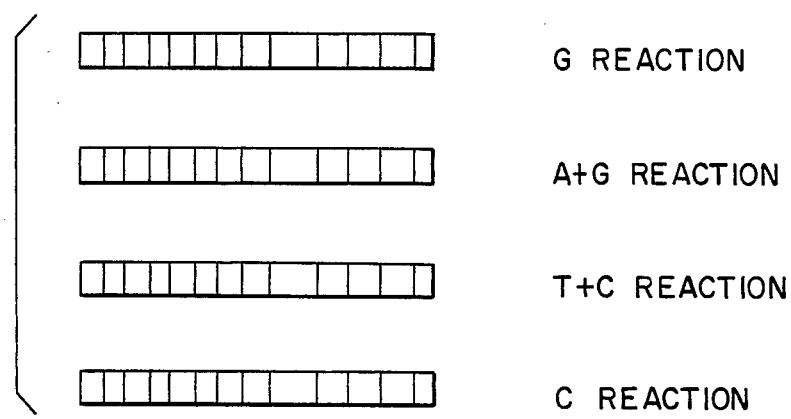

Or n 5'- or 3'-labeled long or short nucleic acid fragments are immobilized on 4 individual but geometrically larger face carriers, so that all n fragments are fixed on a face carrier at a safe distance from each other, as shown in FIG. 2.

All face carriers must be specifically identified. The subsequent washing of the face carrier is performed 2× in succession in water and ethanol, whereby they are relieved of salts or other impurities. Thereafter, they are briefly dried in the air or, if need be, with heated air. For the chemical modification (a) 1 fragment on 4 individual face carriers is subjected to at least 4 different chemical modification reactions (G, A+G, T+C, C). For this purpose on each face carrier (1 to 2 mm×1 to 2 mm) is placed into a specific reaction vessel, for example, microcentrifuge tubes, glass reactor with automatic input and discharge regulation (automat). The face carrier is then treated with excess reagent, i.e, it floats in the reaction medium during the reaction. The following modification reactions may be used: G-reaction with DMS; A+G reaction with formic acid, piperidine formate pH 2 or with diethyl pyrocarbonate; T+C-reaction with sodium permanganate or osmium tetroxide; C-reaction with hydroxyl amine. The face carrier is removed from the reaction vessel manually, for example, by means of a tweezer, after the reaction is completed, or the excess surplus is removed by discharge in the automated system.

(b) n fragments which are applied to 4×n face carriers (immobilized) are sorted out into G, A+G-, T+C- and C-fragments. The n-G, n-A+G, n-T+C and n-C-fragments are subjected in 4 reaction vessels in accordance with (a) simultaneously with excess reagent of the given modification reaction.

(c) 1 fragment on 4 individual face carriers or n fragments on 4×n individual face carriers are not placed in reaction vessels, but applied on chemically inert supports, like glass plates or plastic foils individually and without excess reagent and are then subjected to the 4 individual modification reactions. For this purpose only as much reagents are applied to a face carrier by means of micropipettes so that the support is only wetted (for 1 to 2 mm×1 to 2 mm of a cellulose paper with anion exchange characteristics about 1-5 $\mu l$ reagent).

(d) n fragments are not applied onto 4×n (1 to 2 $mm^2$) large face carriers, but on 4 geometrically larger face carriers in such a manner that all n fragments are fixed on one each face carrier in a safe distance from each other. In accordance with (a) or (c) these face carriers are subjected to the modification reactions with or without a excess reagent. In accordance with (a) larger reaction chambers are required which are adjusted to the 4 geometrically larger face carriers. In accordance with (c), larger volumes for wetting have to be selected.

After completing the modification reactions the chemically modified face carriers are carefully washed 2× in succession with water and ethanol. This is performed manually in that the face carriers are immersed into the corresponding solvent by means of tweezers, they are then placed between blotting paper and dried by applying pressure.

The resulting larger number of face carriers in accordance with (c) can be washed together, but therafter they again have to be sorted out. In automatic systems the carriers in the reactors with the frit are also washed by supplying continuously or discontinuously water and ethanol, after discharging the modification reagents. Subsequently, all face carriers are treated with only one immobilized fragment and individually with a fresh 10% water piperidine solution for 15–45 minutes at 90° C. Thereby, a DNA-strand break occurs and simultaneously the extraction is performed from the carrier. The geometrically larger face carriers with n immobilized fragments are so cut that individual pieces are generated from a larger carrier n. They are are individually treated with piperidine as aforementioned.

For the extraction from the carrier chemical, ionic or electromagnetic agents are used. For ionic extraction high ionic strengths of salts are used, like $(NH_4)HCO_3$, $(NH_4)_2CO_3$, $Et_3NHCO_3$, $Et_3NHAc$, $NH_4Ac$, $K_2HPO_4$ and others.

The process in accordance with the invention has the following advantages:

1. During all of the manipulations an excellent mechanical stability is assured. This mechanical stability in conjunction with the chemical extraction during the piperidine reaction enables complete automation, since no precipitation steps have to be performed in the total process.
2. The mechanical stability of the face carrier opens the possibility to sequence a large number of nucleic acid fragments simultaneously in the reagent surplus, i.e., in the reaction vessel.
3. Due to the chemical extraction during the piperidine reaction an ionic extraction can be avoided, which would require precipitation reactions and therefore causes the loss of short fragments. Short DNA/RNA-oligomers can be advantageously sequenced.
4. Furthermore, the manually as well as the automatic sequencing of large quantities of short and long nucleic acid fragments is made possible.

EXEMPLIFIED EMBODIMENTS

Example 1

Cellulose paper, for example, Whatman 540 paper is activated with cyanuric chloride in accordance with EP 134 025 and is immediately packaged. The paper (5×7) which had been surface treated in this manner is taken out of its special packing (welded foil, which is stored under $N_2$-gassing at $-20°$ C.) and is placed into a glass reaction chamber, wherein 2 mmol (450 mg) triethyl-1-amino-ethyl-ammonium-bromide in 7 ml acetonitrile were previously placed. The reaction chamber is shaken for about 12 hrs. at room temperature. After completion of the reaction paper is repeatedly washed with water and is dried between blotting paper. Instead of the solvent acetonitrile watery buffer systems may be used.

Example 2

400 mg crystalline, nonderivitated cellulose an activation with cyanuric chloride is performed in accordance with EP 134 025 and subsequently reacted in a 25 ml round bottomed flask with 2 mmol (450 mg) triethyl-1-amino-ethyl-ammonium-bromide in 7 ml acetonitrile for 12 hours at room temperature. After the completion of the reaction the cellulose is washed repeatedely with water on a frit and is dried as in example 1.

Example 3

Cellulose (Whatman) 540 paper is surface activated with cyanuric chloride as in example 1 and subsequently placed into a glass reaction chamber, wherein previously 2 mmol (410 mg) 1-bromo-2-amino-ethane-hydrobromide in 7 ml acetonitrile were placed. The reaction is then started by adding 5 ml triethyl amine. The reaction chamber is sealed with a parafilm and is shaken for about 12 hrs at room temperature. After the completion of the reaction, the paper is washed and dried as in example 1.

Example 4

400 mg crystalline nonderivitized cellulose, for example, Whatman is activated with cyanuric chloride as in example 2 and is subsequently reacted in a 25 ml round bottom flask with 2 mmol (410 mg) 1-bromo-2-amino-ethane-hydrobromide in 7 ml acetoneitrile. The reaction is initiated by adding 5 ml triethyl amine and is completed after 12 hrs at room temperature by washing the cellulose and subsequent drying, as described in example 2.

Example 5

Surface activated Whatman 540 paper (5×7) from example 1 is reacted in a reaction chamber with 2 mmol (574 mg) p-amino-benzyl-triethyl-ammonium-bromide in 7 ml acetonitrile for 12 hrs. at room temperature and is further prepared as in example 1.

Example 6

400 mg crystalline surface activated Whatman cellulose in accordance with example 2 is reacted with 2 mmol (574 mg) p-amino-benzyl-triethyl-ammonium-bromide in 7 ml acetoneitrile and further processed as described in example 2.

Example 7

Surface activated Whatman 540 paper (5×7 cm) from example 1 is reacted with 2 mmol (540 mg) p-amino-benzylbromide hydrobromide in 7 ml acetonitrile in a reaction vessel and the reaction is initiated with 5 ml triethylamine. After 12 hrs. at room temperature the paper is washed and dried as in example 1.

Example 8

400 mg crystalline surface activated Whatman cellulose in accordance with example 2 is reacted according to example 4 with 2 mmol (540 mg) p-amino-benzylbromide in acetonitrile and triethyl amine and is washed and dried after the completion of the reaction.

Example 9

Surface activated Whatman 540 paper (5×7 mm) from example 1 is reacted with 2 mmol Glycin-(o-nitromethyl-triethyl-ammonium bromide)-benzylester in 7 ml acetonitrile for 12 hrs. at room temperature in a reaction chamber and further processed as in example 1.

Example 10

Semisynthetic paper of type Hekosyn ® (polyamide and cellulose) is surface activated with cyanuric chloride as in example 1 and subsequently placed into a glass reaction chamber wherein previously 2 mmol (410 mg) 1-bromo-2-aminoethane-hydrobromide in 7 ml acetonitrile were placed. The reaction is then initiated by adding of 5 ml triethyl amine. The reaction chamber is sealed with parafilm and is shaken for about 12 hrs. at temperature. After completion of the reaction the paper is washed and dried as in example 1.

Example 11

Manually sequencing of individual oligonuclotide with chain length of 4 to 15 units

1. Radioactive labeling of the DNA-sequences 10-50 pmol oligonucleotide (or longer fragment) is labeled with the customary processes at the 5'-end with $\alpha^{32}$P-ATP and polynucleotide-kinase. After completing the kinase reaction the total volume is applied to a 20° polyacrylamide-gel, for example, which may contain urea (7M), if need be, and is then separated gel-electrophoretically from ATP and other impurities like the undesirable side products. The desired DNA-band is made visible by a short autoradiography on X-ray film and is cut out from the gel. The gel piece is reduced to small pieces and transferred into an microcentrifuge tubes. The labeled oligonucleotide is recovered by 2× extraction with water between 37° and 60° C. in 30 minutes.

2. Immobilization of the DNA-sequences on the face carrier with anion exchange characteristics 1-2 μl of the water solution obtained under 1 which contains, in addition to the labeled oligonucleotide, salt and urea, if need be, are applied dropwise on at least 4 about 2 mm×2 mm large pieces of the face carrier (example 1-10). After a short drying of the paper pieces at room temperature or with heated air the operation of the dropwise application is continued until about 10 000 to 50 000 cpm per face carrier can be measured on a scintillation measuring device. The papers are subsequently washed in water and ethanol 2× in succession with a tweezer (about 1 min.), and are dried between blotting paper by applying a pressure.

3. Chemical modification reactions for the oligonucleotide d(TCTA), d(TCTAGA), d(GTGAAUUCAC), d(TTCTTCTACACACCC) and d(TGATTCAGAGATGGCTTT) with a excess reagent in the reaction vessel The 4 paper pieces obtained with immobilized labeled fragment of each oliginucleotide in accordance with 2 are placed individually in one each microcentrifuge tubes. The microcentrifuge tubes are marked in accordance with the modification reaction used. A total of 5×4=20 microcentrifuge tubes are present from the 5 oligonucleotides. The following reagents were added by pipettes:
G-reaction—200 ul cacodylate-buffer pH 8 or 200 μl ammonium formate-buffer pH 3.5—1 to 2 μl DMS
A+G-reaction—80 μl 88% formic acid
T+C-reaction—80 μl of a $10^{-4}$M KMnO$_4$-solution, which shortly before had been prepared from a $10^{-2}$M of a stock solution
C-reaction—40 μl of a 4M hydroxyl amine solution pH 6 which was made from hydroxyl amine-hydrochloride by means of a triethyl amine.

The reaction times for the G reaction 10 min. and for all other reactions 20 min. In addition to the mentioned reactions the T+C-reaction may be reacted with osmium tetraoxide (80 μl of a 5 mM OsO$_4$-solution+1 μl pyridine 0.15 min. at 0° C.), the A+G-reaction with piperidine formate (80 μl piperidine formate pH 2, 1 hr.

at 37° C.) or diethyl pyrocarbonate (150 μl A-buffer (50 mM sodium acetate pH 5+1 mM EDTA) +5 to 10 μl of a freshly made 10% DEPC-solution in ethanol, 20 min. at 90° C.). The T+C-reactions with hydrazine inaccordance with Maxam and Gilbert or the A+C-reaction with 1:2M NaOH solution result in the complete loss of the radioactivity and can therefore not be used. During the aforementioned modification reaction the following losses occur: 20% in the G-reaction, 50% in the A+G-reaction, 0% in the T C-reaction and 50-80% in the C-reaction. These are balanced by the double or quadruple radiactivity in the A+G or in the C-reaction. The modification reactions are completed in the papers are removed from the reaction vessels by means of a tweezer and are successively washed 2× with water and ethanol.

Figure 3:
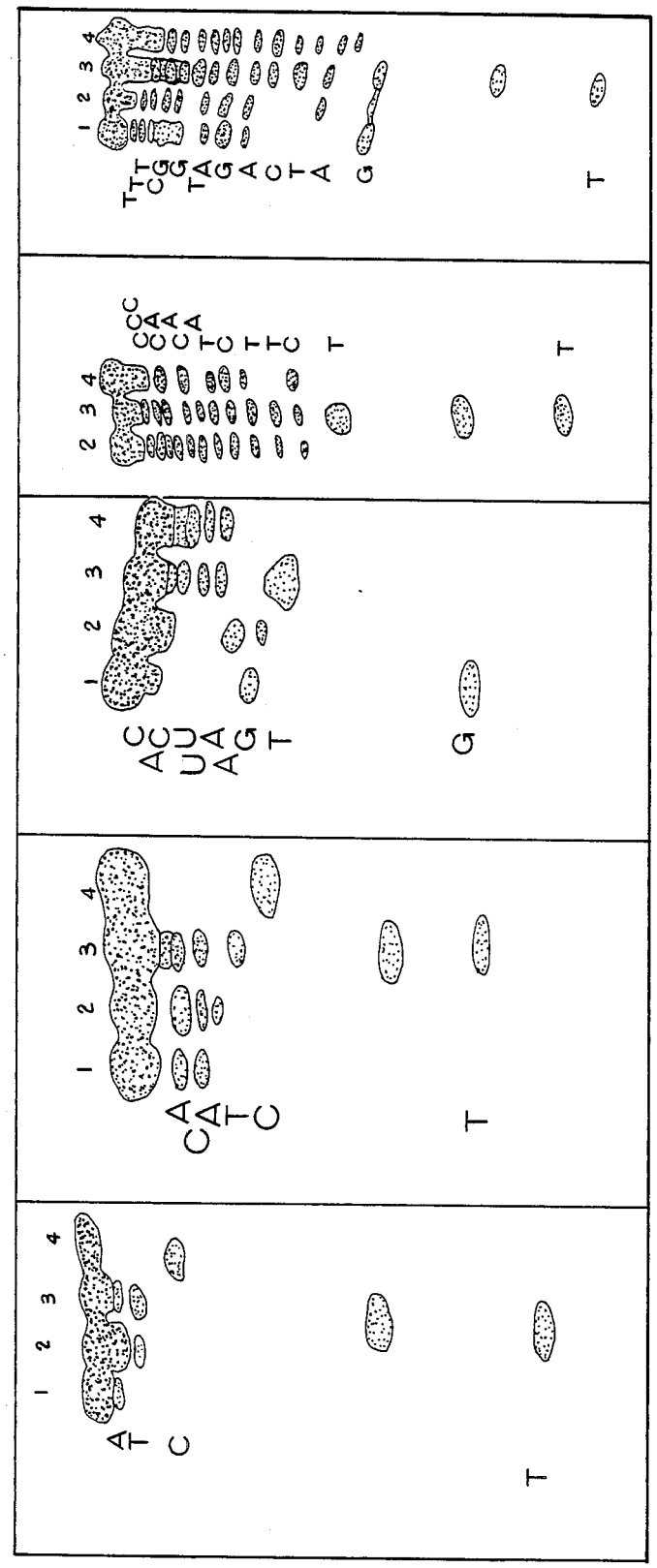
FIGS. 3 and 4 show autoradiograms for sample nucleic acid fragments sequenced by the method of the invention.

4. Piperidine-reaction for making the DNA-strand break and for a simultaneous extraction of the fragments from the carrier The 20 paper carriers are placed individually into 20 new microcentrifuge tubes. After adding 50 μl of a 10% watery piperidine solution they are thermostated for 30 min. up to 90° C. After the completion of the reaction, the papers are removed from the microcentrifuge tubes by means of tweezers, the solutions are stored for 1 min. at −200° C., for example, in liquid air and lyophilized (for about 1 hr.). The lyophilization step is repeated 2× with 10 to 20 μl water (for about 30 min. each). The samples are then ready for application on the gel electrophoresis. Examples of the autoradiograms for the aforementioned oligonucleotide are shown in FIG. 3.

Example 12

Simultaneous manual sequencing of large amounts of oligonucleotides with excess reagent in the reaction vessel Labeling and immobilization of 5 pentadecanucleotides d(TTCTTCTACACACCC), d(TGATCAGATGGCTTT), d(CTCCTGGCCATTCCT) d(GGGTACCCAGAAGTC), and d(TCGCTGAGATCACCA) is performed as described in example 11 (1. and 2.). The chemical modification reactions are now performed in only 4 microcentrifuge tubes, whereby 5 each paper carriers are contained therein. The reaction conditions and the subsequent washing operations are the same as in example 11 (3). After washing and drying of the papers the previously identified carriers are again sorted out, so that again 4 individual papers are present per oligonucleotide, so that they can be individually placed into one each microcentrifuge tubes for the subsequent piperidine reaction. The piperidine reaction was performed analogously to Example 11 (4.).

Figure 4:
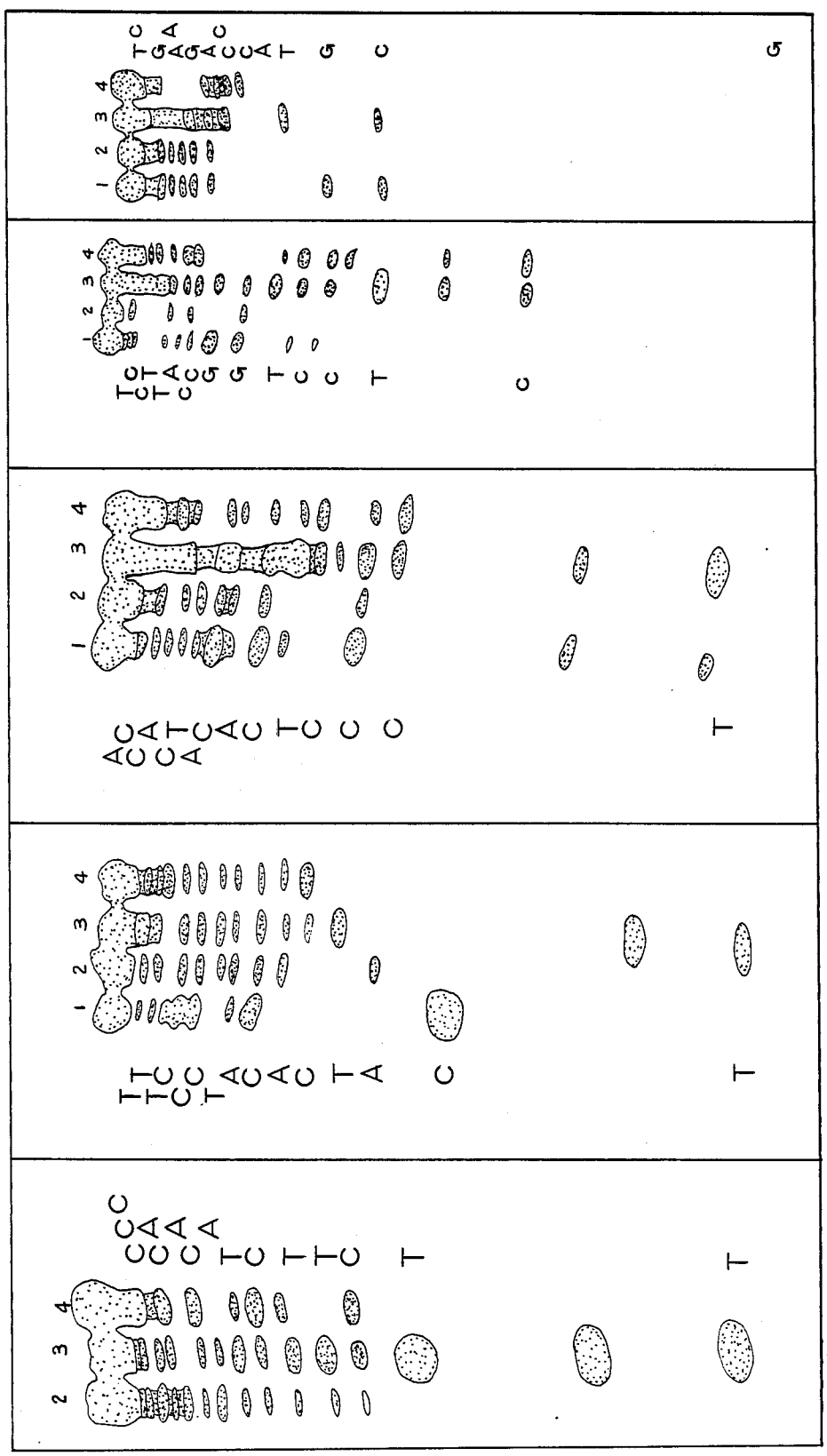

Examples of the autodiagrams for the aforementioned oligonucleotide are shown in FIG. 4.

Example 13

Simultaneous manual sequencing of large amounts of oligonucleotides with excess reagent in reaction vessels The labeling of the 5 pentadecanucleotide of example 12 is performed as described in example 11 (1.). The immobilization of the fragments is not done this time on 4×n (n=5) 20 (2 mm×2 mm) large pieces of the face carrier, but on 4 (2 mm×20 mm) large pieces in such a manner that about 1-2 μl of each oligonucleotides are placed dropwise on a face of 2 mm×2 mm and that all 5 oligonucleotides are placed onto the total face carrier. The 4 larger face carriers are subjected in larger reaction vessels (corresponding to the size of the face carriers to the already described modification reactions. After washing and drying of the carriers the 4 (2 mm×20 mm) large face carriers are cut, with the assistance of a scissor, into 5 smaller (2 mm×2 mm) large paper pieces and placed into 20 microcentrifuge tubes individually and subjected to the piperidine reaction. The piperidine reaction and the lyophilizing is performed as already described.

Example 14

Manual sequencing of long DNA-sequences with reagent surplus in reaction vessels Long DNA-sequences are determined completely analog as in examples 11, 12 and 13. Only the reaction times of the modification reactions listed in example 11 (3.) must be shortened to the following values: G-3 to 5 min. and all other reactions 10 min. The loss of radioactivity is substantially lower with the long DNA-fragments during the modification reactions.

Example 15

Manual sequencing of DNA-sequences without excess reagent

The labeling and immobilization of the DNA-sequences is performed analogously to example 11 (1. and 2.) and 13. The face carriers are not placed into reaction vessels, like microcentrifuge tubes, but are placed onto a plane support covered with a plastic foil and is reacted with only that much volume of the modification reagents (example 11 (3.), that they are just wetted through. Generally, the volumes of 2 mm×2 mm large papers are about 1-3 $\mu$l. If larger face carriers are used, for example, 2 mm×20 mm, the volume of the reagents must be somewhat increased. All other operations like the duration of the modification reactions, washing and the piperidine reaction are performed as already described.

Example 16

Automatic performance of the process

A DNA/RNA-sequencing appratus is constructed as follows. In the simplest case for sequencing of only one nucleic acid fragment, 4 thermostateable reactors equipped with a frit and a capacity of maximum 250 $\mu$l with a dosageable input and discharge are disposed parallel with respect to each other. The 4 individual face carriers (2 mm×2 mm) with the immobilized labeled nucleic fragments are placed into the reactors. Now, the automatic operations in accordance with a predetermined program is performed: (1) washing; (2) chemical modification reactions; (3) washing; (4) piperidine-reaction (extraction). For this purpose the individual reagents are added by means of dosaging pumps in accordance with example 11 (3.) and remain in the reactor with a closed discharge valve for the time determined. After completion of the reactions the valves of the reactors are opened and the reagents discharge, if need be, under a slight air pressure. All washing steps with water and ethanol may be performed continuously (with opened discharge valve the aforementioned reagents are alternately fed into the reactors) or discontinuously (100 $\mu$l volume of the aforementioned solvent are fed into the reactor, whereby the discharge valve is closed and remain there for a short time before they are again discharged). The carriers may be dried for a few seconds, if need be, with heated air at a discontinuous washing or at the end of the continuous washing process. For performing the piperidine reaction about 25-50 $\mu$l 10% of a watery piperidine solution is pumped into the 4 reactors (while the discharge valve is closed) and the reactor or the reactors are heated to 90° C. for 30 minutes. After opening the discharge valve the volumes of the piperidine are blown into 4 individual microcentrifuge tubes under a slight air pressure which are connected by means of teflon hoses ($\phi$0.4-1 mm) with the reactors. The 4 microcentrifuge tubes with the extracted fragments are lyophilized either directly in the automat within a specific vacuum chamber or the lyophilization is performed outside of the system. In the first case the procedure is repeated after the first lyophilization with 10 to 20 $\mu$l water, which is automatically fed, and is repeated (2 to 3 times). The total time of the operation cycle takes about 2.5 hrs. In the second case with the manual lyophilization the total time is about 20-30 min. The samples are then ready for the gel electrophoresis. In the more complicated case for sequencing large amounts of DNA-fragments the 4 reactors must have different spatial dimensions. The base face of a reactor with 8-15 fragments to be sequenced are about 0.5 cm×6 cm. The 4 (0.4 cm×5.5 cm) large face carriers with the applied 8-15 fragments are again placed into the reactors and the operations (1) and (2) are performed naturally with larger volumes of reagents. After discharging the reagents of the modification reactions a washing (operation 3) is performed. Thereafter, the dried face carriers are automatically cut into smaller pieces by a defined relized technical principle and are simultaneously transferred into different piperidine reactors provided with a frit and a discharge valve (about 50 reactors). This is performed by the construction of 4 movable modification-reactors, which lower by 180° after operation (3) and then open on the reactor lid. The face carriers are thereby brought into 4 moveable (vertically displacement) cutting devices. By cutting off small pieces from the face carriers in the 4 vertically displaceable cutting devices the 4×8 to 15=32 to 45 piperidine reactors are charged with only 1 fragment in a controlled manner.

The piperidine reactions are performed analogously, as already described. After completing the reaction the piperidine solutions with the extracted fragments transferred by means of a slight air pressure into the microcentrifuge tubes (about 50 pieces) which are connected with the reactors by means of teflon hoses and are subsequently lyophilized.

Example 17

Sequencing by use of high ion strengths for extracting the nucleic acid fragments from the carrier When using the described face carriers the extraction of the fragments before the piperidine reaction may also be performed with 1 to 2M solutions of the salts of $NH_4HCO_3$, $(NH_4)_2CO_3$, $NH_4Ac$, $EtNHAc$, among others. The extraction is achieved in that the face carriers are individually reacted in reaction vessels, like the microcentrifuge tubes, 2× with 50 $\mu$l of the aforementioned salt solutions at 60°. With the obligonucleotides the extractions are lyophilized, whereby the salts are evaporated during a repeated lyophilization with watery ethanol. With long DNA-fragments the salts may be removed by means of ethanol-precipitation. Thereafter, the customary piperidine-reaction is performed in a homogenic phase.

We claim:

1. A process for sequencing a nucleic acid fragment by chemical degradation in a solid phase which comprises the steps of:
   (a) immobilizing labelled nucleic acid fragments in an aqueous solution on a solid support, said solid support having a high mechanical stability and anion exchange properties, as well as the ability to undergo a step of simultaneously cleaving said nucleic acid fragments immobilizing thereon and chemically eluting degraded nucleic acids from the solid support;
   (b) washing the labelled nucleic acid fragments immobilized on said solid support during step (a);
   (c) chemically modifying organic, heterocyclic nitrogen bases selected from the group consisting of thymine, quanine, cytosine, adenine and uracil, which form part of the nucleic acid fragments, so that a base specific chemical reaction corresponding to each nucleic acid residue in the sequence takes place;
   (d) washing the labelled nucleic acid fragments immobilized on the solid support and chemically modified during step (c);
   (e) sorting the labelled nucleic acid fragments;
   (f) simultaneously chemically cleaving the backbone of the nucleic acid fragments and chemically eluting degraded nucleic acids from the solid support;
   (g) lyophilizing the degradated nucleic acids; and
   (h) determining the sequence of the nucleic acid fragments by subjecting the degradated nucleic acids to electrophoresis.

2. A process for sequencing a nucleic acid fragment by chemical degradation in a solid phase which comprises the steps of:
   (a) immobilizing labelled nucleic acid fragments in an aqueous solution on a solid support, said solid support having a high mechanical stability and anion exchange properties, as well as the ability to undergo a step of simultaneously cleaving said nucleic acid fragments immobilized thereon and chemically eluting degraded nucleic acids from the solid support, said support comprising the reaction product of a macromolecular carrier which comprises:
      (i) 5 to 80% by volume of a macromolecular compound;
      (ii) 1 to 80% by volume of a macromolecular compound having 4,6-dihalogen-1,3,5-triazine groups;
      (iii) 0.5 to 50% by volume of a 2,4,6-trihalogen-1,3,5-triazine;
      (iv) up to 20% by volume of a halide; and
      (v) up to 5% by volume of buffering agents; and an amine salt of the Formula (I)

$$\left[ X-R-N \begin{array}{c} R^1 \\ R^2 \\ R^3 \end{array} \right]^+ Y^-$$

wherein
   X is an $NH_2$, OH or SH group;
   R is $C_1$ to $C_{10}$ alkyl, benzyl or a photochemically cleavable group selected from the group consisting of an o-nitrobenzene ester, a methylphenacyl ester and a heterocyclic group;
   $R_1$, $R^2$ and $R^3$ are each hydrogen or $C_1$ to $C_3$ alkyl; and
   Y is halide or hydroxyl;
   (b) washing the labelled nucleic acid fragments immobilized on said solid support during step (a);
   (c) chemically modifying organic, heterocyclic nitrogen bases selected from the group consisting of thymine, guanine, cytosine, adenine and uracil, which form part of the nucleic acid fragments so that a base specific chemical reaction corresponding to each nucleic acid residue in the sequence takes place;
   (d) washing the labelled nucleic acid fragments immobilized on the solid support and chemically modified during step (c);
   (e) sorting the labelled nucleic acid fragments;
   (f) simultaneously chemically cleaving the backbone of the nucleic acid fragments and chemically eluting degradated nucleic acids from the solid support;
   (g) lyophilizing the degradated nucleic acids; and
   (h) determining the sequence of the nucleic acid fragments by subjecting the degradated nucleic acids to electrophoresis.

3. The process for sequencing a nucleic acid fragment defined in claim 1 wherein the amine salt of the Formula (I) is prepared in situ by reacting a salt of the Formula (II)

$$Y^- - [NH_3-R-Y]^+$$

with a compound of the Formula (III)

$$N \begin{array}{c} R^1 \\ R^2 \\ R^3 \end{array}$$

4. The process for sequencing a nucleic acid fragment defined in claim 1 wherein in the salt of the Formula (I)
X is amino;
R is $C_1$ to $C_{10}$ alkyl or benzyl; and
$R^1$, $R^2$ and $R^3$ are each $C_1$ to $C_3$ alkyl.

5. The process for sequencing a nucleic acid fragment defined in claim 1 wherein the step of simultaneously chemically cleaving the nucleic acid backbone and chemically eluting the degradated nucleic acid fragments is carried out with an aqueous solution of piperidine.

6. The process for sequencing a nucleic acid fragment defined in claim 2 wherein in the salt of the Formula (I) X is amino, R is an o-nitrobenzene ester, $R^1$, $R^2$, and $R^3$ are each ethyl, and Y is bromide.

* * * * *